United States Patent [19]
Blum et al.

[11] Patent Number: 4,686,624
[45] Date of Patent: Aug. 11, 1987

[54] PORTABLE APPARATUS FOR ACQUIRING AND PROCESSING DATA RELATIVE TO THE DIETETICS AND/OR THE HEALTH OF A PERSON

[75] Inventors: Dominique Blum, 14, rue due Vallon, Thise, 25220 Roche Lez Beaupre; Pierre Grandmottet; Pierre Bechtel, both of Besancon, all of France

[73] Assignee: Dominique Blum, Paris, France

[21] Appl. No.: 598,709

[22] Filed: Apr. 10, 1984

[30] Foreign Application Priority Data

Apr. 12, 1983 [FR] France ................................ 8305949

[51] Int. Cl.⁴ .................. G06F 15/42; G06G 7/60; G01D 9/00
[52] U.S. Cl. ................................. 364/415; 364/413; 346/20
[58] Field of Search ............... 364/413, 415, 417, 418, 364/709, 715, 187, 146, 705; 371/10, 66; 346/20, 33 R, 33 ME; 340/573

[56] References Cited

U.S. PATENT DOCUMENTS

| | | | |
|---|---|---|---|
| 4,095,274 | 6/1978 | Gordon | 364/413 X |
| 4,192,000 | 3/1980 | Lipsey | 364/415 |
| 4,212,079 | 7/1980 | Segar et al. | 364/415 X |
| 4,244,020 | 1/1981 | Ratcliff | 364/413 |
| 4,281,330 | 7/1981 | Warrick | 346/20 |
| 4,321,674 | 3/1982 | Krames | 364/413 |
| 4,323,987 | 4/1982 | Holtz et al. | 371/10 X |
| 4,491,725 | 1/1985 | Pritchard | 364/413 X |
| 4,527,240 | 7/1985 | Kvitash | 364/415 |
| 4,575,804 | 3/1986 | Ratcliff | 364/413 |

Primary Examiner—Jerry Smith
Assistant Examiner—Jon D. Grossman
Attorney, Agent, or Firm—Larson and Taylor

[57] ABSTRACT

The portable apparatus for acquiring and processing information relative to the dietetics and/or health of a person comprises, in combination, a series (2) of alphanumeric keys for inputting information relative to the dietetics and/or the health of the user; at least one ROM in which are stored data and instructions in relation with this information; a display (5) for displaying the information introduced and the indications relating to them coming from the ROM; and a device for effectively inputting (3e) and refusing inputting (3d) of this information. The device also comprises a clock for dating each input of information; at least one RAM adapted to store the inputted information as well as the date thereof; a computing adapted to determine, from the inputted information and from data stored in the ROM, instructions intended for the user of the apparatus and relative to the dietetics and/or health of the user; main electric power supply for the apparatus; and a communication device (11) for transferring information stored in the RAM to an external data processing unit and, in return, the introduction into this RAM of instructions coming from this unit.

5 Claims, 6 Drawing Figures

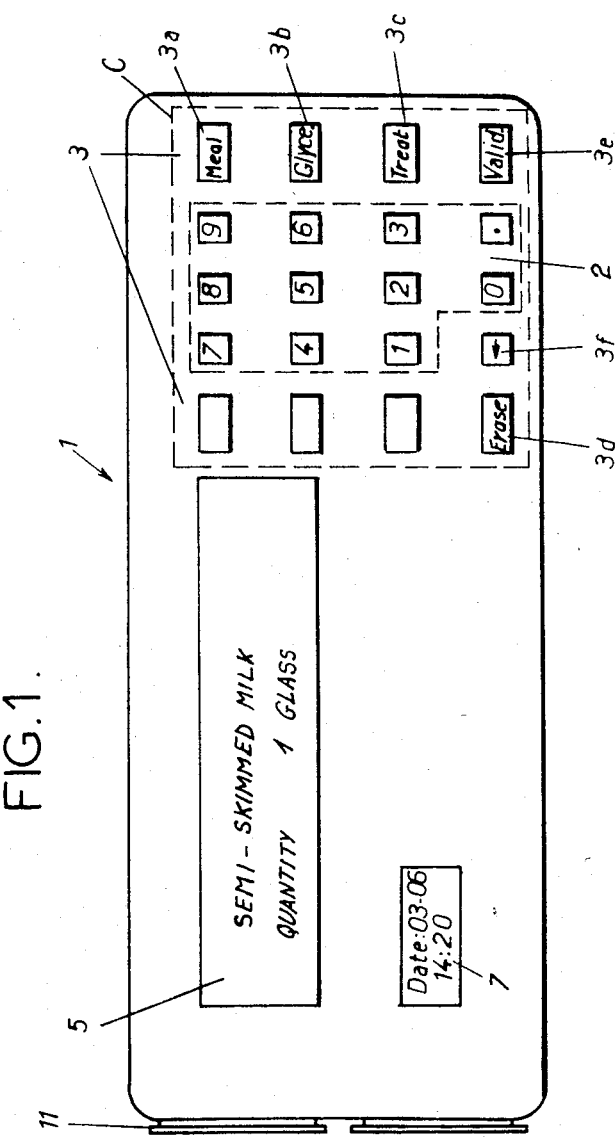

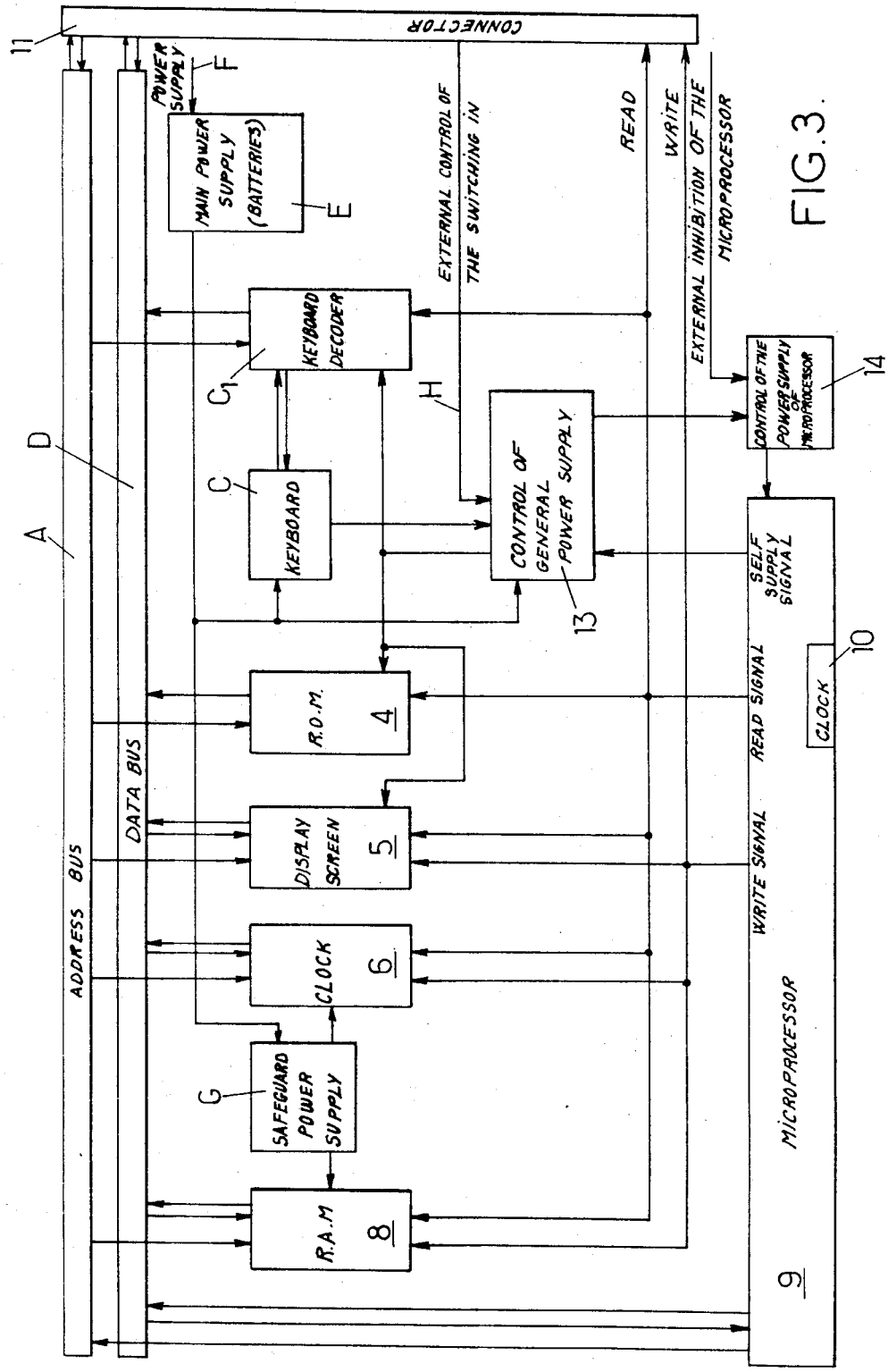

PORTABLE APPARATUS FOR ACQUIRING AND PROCESSING DATA RELATIVE TO THE DIETETICS AND/OR THE HEALTH OF A PERSON

The present invention relates to a portable apparatus for acquiring and processing data relative to the dietetics or the health of a person.

The invention relates more particularly, but not exclusively, to persons subjected to supervision of their food diet or persons subjected to a medical treatment, such as diabetics.

The aim of the invention is especially to provide apparatus which allows the persons concerned to follow the dietetic and/or medical prescriptions more easily, to take into account repetitive data and to be able to communicate the latter to the doctor in attendance or to a supervising body.

From the U.S. Pat. No. 4,321,674 a device is known capable of cumulating and displaying the number of calories corresponding to the food and/or the drink taken by the user. This known device comprises:

a certain number of data introducing keys, some corresponding to the main types of food and/or drinks, and the others providing validation or cancelling of data introduction;

means for displaying the carbohydrate, protein, fat and calorie contents of the food and/or of the drinks considered, and at the same time the typical daily proportions of these constituents in foods and drinks;

keys for introducing these typical daily proportions; food/drink switching means; and appropriate storage and computer means.

Moreover, the user has a table of the different types of food informing him which keys he should actuate and how many times, depending on the nature and the amount of the food or drink.

This is a simplified device only giving approximate values of the carbohydrates, protein and fat and calorie contents of meals, the number of the types of food and/or drinks being greatly reduced; with this device, the user must refer to a table with the composition of foods, whereby there is a risk of errors in determining the key to be actuated and the number of times it must be actuated so as to take the amounts into account.

Furthermore, it does not allow the times when meals are taken to be taken into account, nor the nature and amounts of the different foods and drinks consumed by the user to be stored, nor finally the data to be transferred to another unit, such as a computer, for checking and supervision by a doctor or an organisation.

The U.S. Pat. No. 4,281,330 describes a device for supervising and recording medical treatments with keys for the different treatments, different medicaments and the amounts of medicaments. A clock is provided. The treatments, medicaments, amounts and times are processed in a microprocessor of the device, then transmitted for recording to a thermal printer and a magnetic tape recorder, this latter also receiving the indications from an electrocardiograph.

It will be noted that in these two known devices:

the keys are permanently preassigned to one type of food or drink, in one, or to a treatment, medicament, an amount, in the other, without possibility of development or modification, the first device being purely dietetic and the second purely medical;

no provision is made for storing the input data, but only of the results elaborated from these inputs;

the direct transfer of the whole of the data introduced with the date of this introduction cannot be transferred to another unit, such as a computer, likely to be used by a doctor or a supervising organisation for supervising the dietetics and/or the health of the user and to establish prescriptions for this latter.

The object of the present invention is to palliate the above mentioned drawbacks by providing a portable self contained and personnalisable apparatus for introducing a large number of very precise data concerning the nourishment and/or the medical treatment of a person, for memorizing this data with the time at which they are introduced and transferring this data with their time of introduction to another unit.

To this end, the portable apparatus for acquiring and processing data relative to the dietetics and/or the health of a person, according to the invention, is characterized by the fact that it comprises, in combination, a series of alphanumeric keys inputting information relative to the dietetics and/or the health of the user; at least one read only memory (ROM) in which data and instructions in relation with this information are stored; means for displaying the information introduced and indications concerning them coming from the ROM; means for effectively inputting and refusing the inputting of this information; clock means for dating each information input; at least one random access memory (RAM) adapted to store the inputted information as well as its date; computing means adapted to determine, from the inputted information and from data stored in the ROM, instructions intended for the user of the apparatus and relative to the dietetics and/or the health of the user; main electric power supply means of the apparatus; and communication means for allowing information stored in the RAM to be transferred to an external data processing unit, as well as in return the introduction, into this RAM, of instructions coming from said unit.

The display means may also be used for displaying the instructions contained in the RAM.

The inputting of information, by tapping on the key board, may be achieved by means of a ciphered code or a mnemonic code; it is then advantageous to provide on the apparatus itself, for example at the back of the apparatus, a glossary for establishing the correspondance between the clear language information and the ciphers of the code. For example, in the case of a food diet, the glossary will give the correspondance between each food concerned and the ciphers of the code.

When the apparatus is intended for persons bound to a food diet, for example diabetics, the ROM contains data relative to a certain number of foods, this data being formed more especially by the average proteid, lipid, glucid, alcohol and calorie content of the food in question, and the computing means are adapted so as to determine, for each food, depending on the amount which will be absorbed, the amount of proteids, lipids, glucids, alcohol and calories.

The qualitative and quantitative detail of the meal is stored, with its data, in the RAM. This RAM may further contain personalized information which is entered, for example, during a medical consultation and which relates to the daily reference amounts of proteids, lipids, glucids, alcohol and calories which may be consumed by the person concerned and the computing means will cause to be displayed before each information input relative to a meal or to food absorption, the available proteid, lipid, glucid, alcohol and calorie credit for the current day; these computing means modify, during the day, the available credit depending on the information introduced; this available credit is reset to its reference value at a given time, for example at midnight, for the following day.

Advantageously, the keyboard for introducing the data relating to dietetics and/or health in an apparatus intended for example for diabetics, comprises a "meal" key, a "glycemia" key and a "treatment" key, and the apparatus is adapted so that when the user has pressed one of these three keys, the apparatus is switched on and the information subsequently introduced by the user by means of the alphanumeric keys of the keyboard is processed by the apparatus as being relative either to the composition of a meal, or to the glycemia (dosage of glucose), or to the prescribed medical treatment, so as to supply the corresponding instructions.

The portable apparatus advantageously comprises means for connection to a micro computer or similar for transferring the information stored in the RAM from the apparatus to the micro computer with a view to analysing it, the RAM being reinitialized after this information has been transferred, the storage time of the information in the portable apparatus being greater than the average time interval which separates two connections of the apparatus to the micro computer. In return, the micro computer may introduce instructions and/or data into the RAM of the portable apparatus.

The computing means comprise a microprocessor.

The invention will be better understood from the following description of a particular embodiment, with reference to the accompanying drawings.

FIG. 1 of these drawings is a top view of an apparatus in accordance with the invention;

FIG. 2 is a left hand view with respect to FIG. 1;

FIG. 3 is a block diagram of the apparatus; and

Figure 4A:
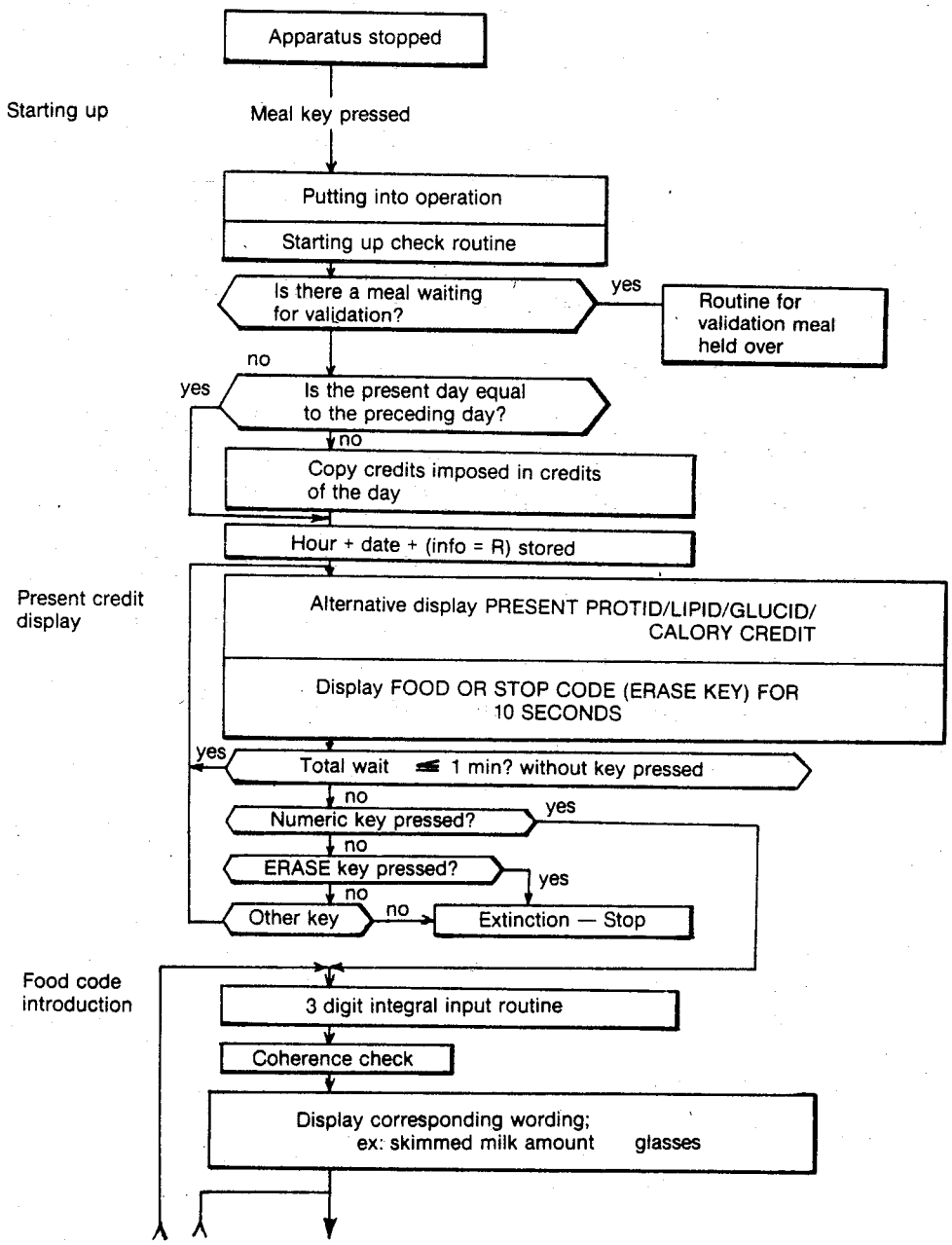
Figure 4B:
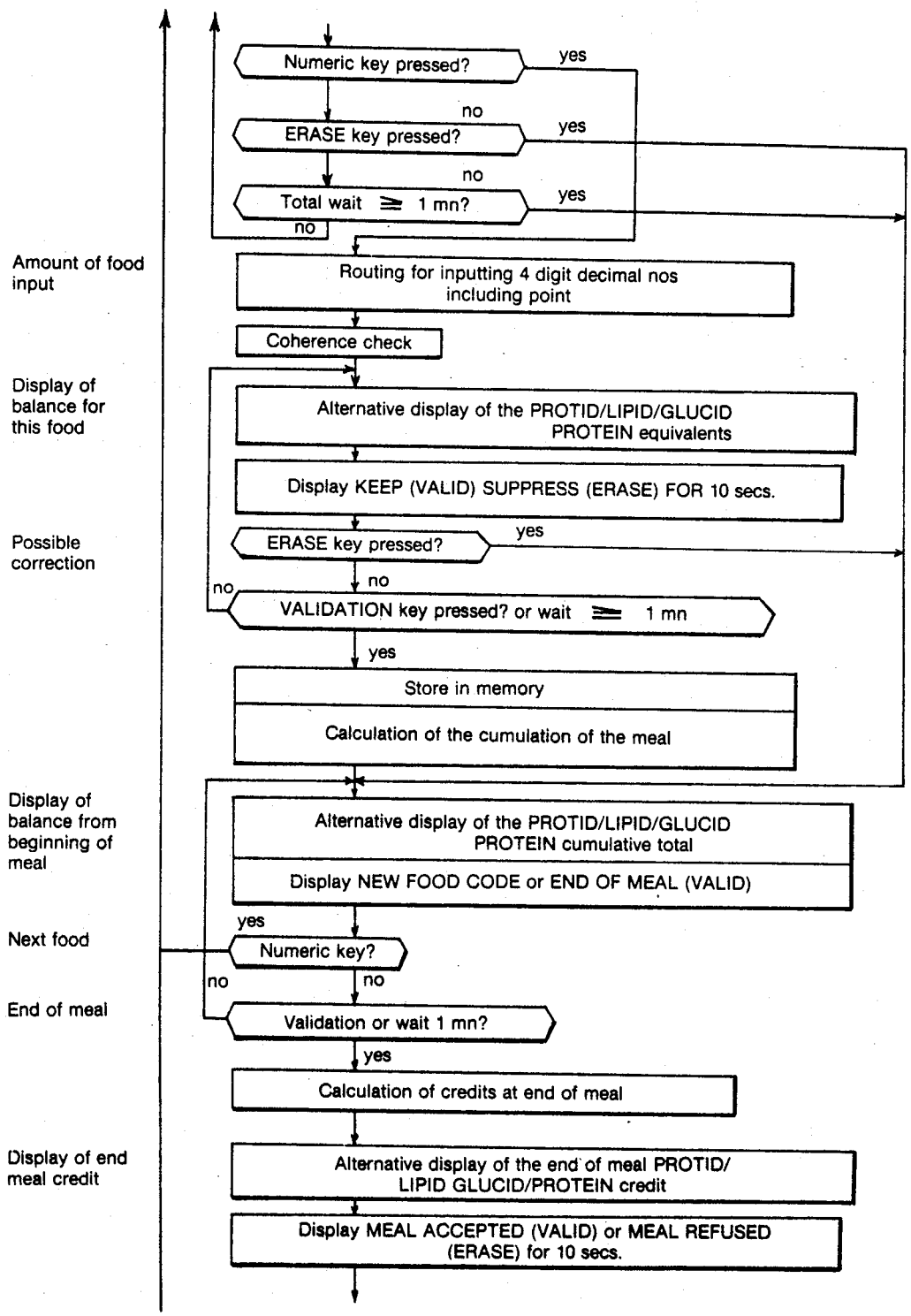
Figure 4C:
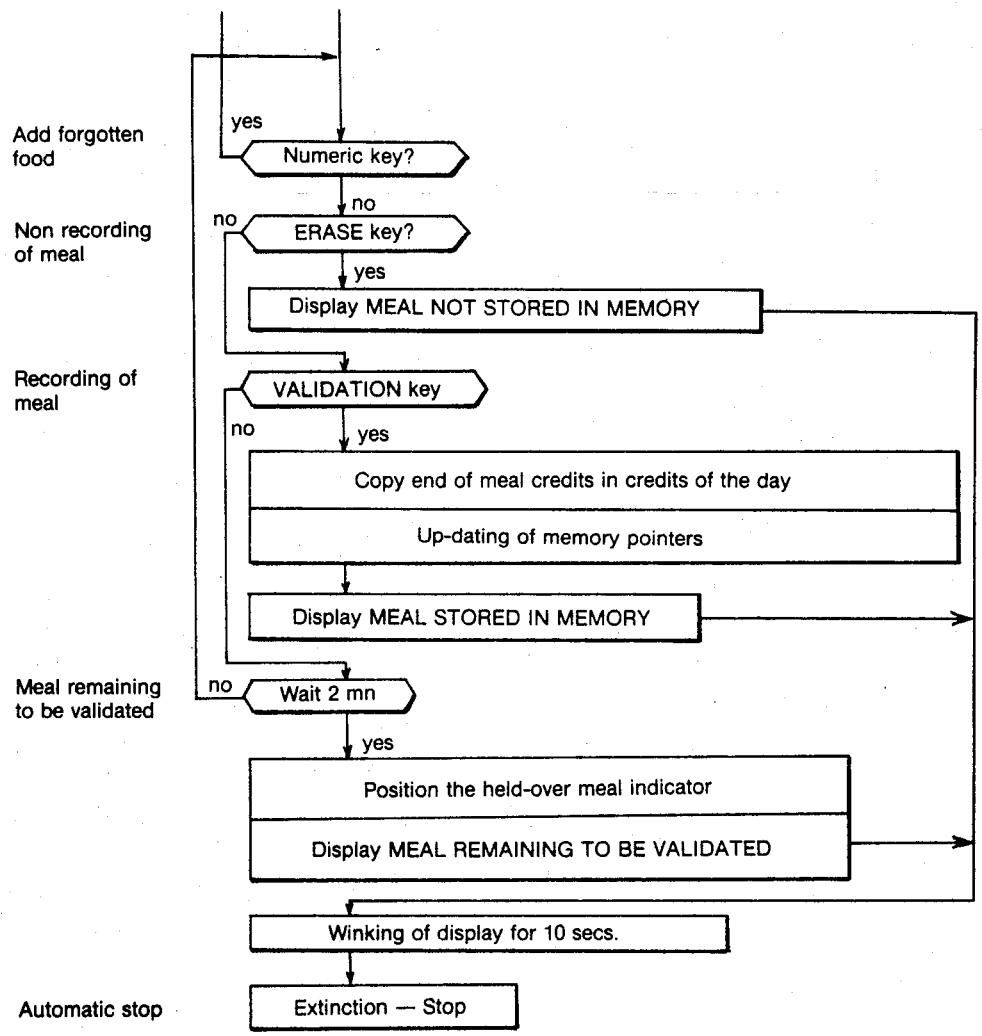

FIGS. 4(a), 4(b) and 4(c), taken together, constitute a flow chart for a particular program.

Referring to FIG. 1, a portable apparatus 1 is shown of the pocket calculator type for acquiring and processing information relative to the dietetics and/or the health of a person. In particular, the exemplary apparatus 1 shown is intended for diabetic persons undergoing treatment and a given diet or, more generally, for persons on a diet, followed more especially by an organisation of the "weight watchers" type.

The apparatus comprises means for inputting information relative to the health, formed by a keyboard C with a series of alphanumeric or even numeric keys 2 and a series 3 of specialized keys. The alphanumeric part 2 of the keyboard C shown in FIG. 1 comprises essentially figures for, in the exemplary apparatus illustrated, the information is introduced by means of a ciphered code. A glossary (not shown) may be provided on the back of the apparatus for establishing the correspondance between the clear language information and the figures of the code, the apparatus displaying in any case the clear language wording corresponding to the code introduced, as indicated hereafter.

Three specialized keys 3a, 3b and 3c are provided for processing, in apparatus 1 information relative to different operations, either to meals (key 3a), or to glycemia, i.e. to the glucose content of the blood (key 3b), or to a medical treatment (key 3c).

The apparatus is designed so that, when one of these specialized keys 3a, 3b, 3c is pressed, it is switched on and is operative for processing information relative to the operation corresponding to the key which has been pressed.

An ROM 4, shown schematically in FIG. 3, is provided and contains different instructions and data, among which is provided a table of the foods (with an 8 bit code 256 different foods and drinks may be stored), with the mean proteid, lipid, glucid and alcohol composition of each food or drink entered; other instructions and data, explained further on, are also stored in the ROM 4.

A screen 5 (FIG. 1) is provided for the display.

Apparatus 1 further comprises clock means 6 (see FIG. 3), formed more especially by a time base for dating each information input; these clock means give the dafe, the day, the hours and the minutes or else are graduated in quarter hours ($24 \times 4 = 96$ graduations per day); if required, a permanent external display may be provided, shown in a rectangle 7 in FIG. 1, of the hour given by the clock means 6.

A RAM 8 (FIG. 3), having a sufficient capacity, is provided for storing information inputted by keyboard C and corresponding dates, for a predetermined time of 45 days for example. This memory 8 is also intended to store evolutive program portions corresponding to data peculiar to the user.

Computer means 9 (FIG. 3), formed advantageously by a microprocessor, are provided for determining, from the information inputted by keyboard C and instructions and data stored in ROM 4, instructions intended for the user of the apparatus relative to the dietetics and/or the health of the user, these instructions appearing on the display screen 5.

The ROM 4 contains, in addition to the fixed data, more especially those relative to the foods, the monitor program controlling the microprocessor 9.

The data flows over a data bus D, whereas the addresses flow over an address bus A.

Apparatus 1 is further equipped with a connector 11 (FIGS. 1, 2 and 3) for connecting with an interface: apparatus 1/computer in particular microcomputer) and possibly a connector (not shown) for connection with a glycemic analyser.

Microprocessor 9 is provided with its own quartz clock 10 for controlling the operations, but which does not have a function of dating the input of data, which function is provided by clock 6.

So as to facilitate the acquisition of data, there are provided, in the series 3 of specialized keys, in addition to the above mentioned keys 3a, 3b, 3c, an "erase" key 3d for erasing the information which has just been entered on keyboard C and which appears on screen 5, "validation" key 3e for validating this data, after a visual check (on screen 5) of the information entered, and for inputting it into the RAM 8, and a key 3f, shown with an arrow in FIG. 1, for effecting corrections, with keyboard C is associated a keyboard decoder C1.

The internal clock means 6 not only allow each information collected to be dated but also make the aid memoire function possible, for example by recalling, by means of a sound or visual "winking" alarm, the schedule of a treatment, or a glycemic check for a diabetic, the date of the appointment for consulting a doctor or a supervising (weight watcher) organisation, etc.

The ROM 4 contains the monitor program controlling the general functions of the calculator: management of the keyboard, management of the display, possibly continuous display of the time, supervision of the room available in the ROM 8, management of the peripherals etc.

The ROM 4 further comprises programs corresponding to three specialized keys 3a (meals), 3b (glycemia) and 3c (treatment).

1. Should the "meal" key 3a be actuated, the calculator will operate in accordance with the "dietetic" program of the ROM 4. When the ciphered or mnemonic code of a food is entered with the keyboard, the name of this food (for example semi-skimmed milk, as shown in FIG. 1), possibly abbreviated, appears displayed in clear language on screen 5. The program of the ROM 4 then requests the amount absorbed, in a current unit of measurement which may, for example in a very practical way, be a soup or coffee spoon or a glass as indicated for example in FIG. 1). Each food absorbed, referenced by an internal 8 bit code (possibility of cataloguing 256 foods) is stored (in the RAM 8, in this form with the amount and date).

Thus, at the time of the meal, the person concerned records the composition of the meal and obtains the total proteid, lipid, glucid, alcohol and calorie amount thereof which appears on screen 5. Several tests of the composition of meals may be effected, before validating, by pressing key 3e, the composition of a meal and before consuming this meal.

Cumulated over 24 hours, these results allow the daily food rations to be balanced. After each meal, the remaining proteid, lipid, glucid, alcohol and calorie credit is automatically determined by the calculator by deducting from the preceding credit the composition of the meal which has just been stored in memory. When the "meal" key 3a is actuated, the present proteid, lipid, glucid and calorie credit appears on screen 5.

Every day, that is to say every 24 hours, at a definite time given by the internal clock 6, for example at midnight, the daily food credit is reset to its initial value, which value will have been prescribed by the doctor or a supervising organisation, for example during a consultation or a preceding meeting, and introduced into the RAM 8 through the connector 11.

The automatic computation, by apparatus 1, of the proteids, lipids, glucids, alcohol and calories of a meal is effected by means of the table stored in the ROM 4, in which each food or drink comprises its average and approximate proteid, lipid, glucid and alcohol composition. The calorie calculation is made from this data.

The balance for each food may be obtained displayed on screen 5 and a coding error may be cancelled out at any time.

The summation is effected for the whole of the meal, and the difference in excess or in deficit with respect to the theoretic diet, as explained above, remains known until the next meal. The complete composition of the meal, associated with the schedules supplied by clock 6 is stored in the RAM 8.

It should be noted, in so far as supervision of nourishment is concerned, that there exists certain private or public extra-medical associations or organisations which attempt to help people having nutrition troubles, obesity, etc.

One example originating in the United States, has developed in numerous countries: it is a question of the "weight watchers" association which has gained numerous followers.

These associations give to their members the maximum means for helping them to fight against dietetic errors, and periodic meetings are arranged for analysing the progress of each one and possible nutritional errors.

The calculator of the invention, with suitable computing and storage means, allows the amount of lipids, proteids, glucids, alcohol and calories of each meal, introduced dish by dish by means of the keyboard, to be accurately evaluated.

This information may be stored in the RAM of the calculator; and, during a periodic meeting, a systematic analysis for each participant may be drawn up by the association's computer, by means of connector 11 of the calculator.

Since this information is stored with a date and time of its introduction by means of the keyboard, the "dietetic chronology" may even be reconstructed, since a large number of nutritional troubles are related to feeding schedule problems (snacks, nibbling, missed meals).

2. Actuation of the "glycemia" key 3b brings into play the corresponding program stored in the ROM 4. The value of the glycemia (glucose content of the blood) may be introduced manually by the person concerned who inputs by means of clavier C the value which he or she has determined by means of a rapid quantity determination means with which he or she is provided. According to another possibility this value of a glycemia may be introduced automatically, by means of a glycemic analyser which would be connected to a connector (in addition to connector 11), not shown, provided on the calculator. The value of the gylcemia appears on the screen 5 of the calculator, whether it is introduced manually or automatically. The person concerned validates the value displayed, by pressing the "validation" key 3e. The result of the measurement, as well as the schedule supplied by the internal clock 6, are then stored in the RAM 8.

As previously mentioned, the apparatus 1 may provide an automatic reminder of the timetable for the glycemia check.

3. In the case of a person undergoing medical treatment, for example in the case of a diabetic, apparatus 1 may also give a reminder, by means of a visual or sound alarm, of the timetable for taking anti-diabetic medicaments or for insulin injection. The user, after having pressed the "treatment" key 3c, may record the type of treatment and the dose of medicament absorbed or insulin injected. This information is stored in the RAM 8 as well as the time and the date at which this treatment was carried out. Generally, the accessory functions, such as the reminder of the date of the next consultation, the intermittant display of particular information, may be provided by a specific program using the RAM 8.

All the information introduced (composition of the meal, glycemic value, type and dose of treatment), associated with the corresponding timetables are therefore stored in the RAM 8 of the calculator. The whole is designed so as to automatically suspend operation, without loss of information, if the storage capacity of memory 8 is exceeded.

At the time of the next consultation, by connecting to connector 11, through an appropriate interface, all the information stored in the RAM 8 is transferred to the computer of the doctor who may then have the data processed instantaneously or postpone the processing.

Given a monthly rate of consultation, a storage possibility for a minimum of 45 days is provided, so as to take into account possible postponements of appointments.

At each medical consultation, the information stored in the RAM 8, relative to foods, to glycemia and to the taking of medicaments, are erased after being transferred into the doctor's computer, so that the RAM 8 is ready for new recordings.

It should be noted that the apparatus 1 is "personnalized" at the very time of its first use, during the first consultation. This personnalisation consists in introducing into the RAM 8 information relative to the person concerned, in particular: name of this person, characteristics of the food diet, of the medicaments and treatments prescribed, date of the present consultation and of the next consultation, etc.

This information may be updated by the doctor during subsequent consultations.

The time base 6 may be adapted so that its output allows the dates to be memorized, quarter of an hour by quarter of an hour, from a "zero" date input into the storage memory from the computer of the doctor, this "zero" date being recorded at each appointment. For a period of 45 days, the quarter of an hour time intervals represent then about 4500 periods which may be stored. At each consultation, the exact date is corrected at the same time as the start of the time counting is initiated.

The display screen 5 comprises, in addition to a signalling reference system, at least one line of 30 alphanumeric characters for writing in clear language the foods and the amount absorbed, and more generally any information inputted by the keyboard and any instruction given by the apparatus.

Preferably, the ROM 4 and the RAM 8 each have a capacity of 1 K Bytes.

Apparatus 1 is equipped with a double power supply system by means of rechargeable batteries E, thus providing independent operation. Apparatus 1 may, if required, be provided so as to operate also from the mains F. Advantageously a possibility is provided for testing the state of charge of the batteries and for controlling the general power supply at 13 and the power supply of the microprocessor 14.

The RAM 8 remains supplied, from a second battery G (safeguard power supply), even if the calculator is not used, and even when the main battery E is discharged.

For determining the quantity of glucose in the blood, an automatic apparatus with digital display may be used such as are commercially available, for example the one known under the name "AMES glucometer".

The connector 11 of the calculator/computer interface is provided for matching the different computers generally used in medical surgeries. It is compatible with the transmission standards for micro-data processing.

Control of switching on and of sharing the buses by the interface is advantageously provided as follows.

A first electronic circuit, supplied permanently with power by the battery E of the apparatus, receives control information:
from the keyboard C itself permanently supplied with power
from the microprocessor 9
from the interface connector 11.

A. In portable use, actuation of keyboard C activates this circuit, which then drains the current towards the assembly of components, except the microprocessor 9. Among these components, a second control circuit is fed with current from this time on. This second circuit receives additional control information from the interface collector 11, depending on which it conducts the currents towards the microprocessor 9 or not.

First case: the information is absent; then the second circuit is conducting and microprocessor 9 starts to operate; the internal program proceeds and then controls a signal which returns to activate permanently the first circuit, so that this latter remains conducting: it is "self-feed": then the keyboard C may be released, and the microprocessor continues its activity until the time when it cuts off its self supply signal.

Second case: the information is present; in this case the second circuit remains non conducting and microprocessor 9 does not start operating; the whole of the power supply is cut off as soon as keyboard C is released.

B. In use via the connector 11, the interface may play the role of the keyboard by activating the first circuit. If it does not give the information described above, microprocessor 9 is activated (see first case above).

On the other hand, if the interface gives this information, the microprocessor 9 is not activated, whereas all the other components are live and functional. The interface, through the connector 11, since it has available the control line H, the data bus D and the address bus A, is consequently able to use all the resources of the calculator, without interference with the signals of the microprocessor 9 thereof which it inhibits.

It is clear that the calculator 1 of the invention may be used and adapted to other types of information relative to the nutrition and/or health of a person. For example, such an apparatus could be adapted to information relative to the blood pressure, and to the rate of heart beat.

As non limiting examples of circuits used in the apparatus, the following references may be mentioned:
ROM 4: reference 23C64 Hughes
RAM 8: reference TMM 20C64 Toshiba
Microprocessor 9: reference 80C51 Intel
Display screen 5: EPSON EA-Y 20O25 AZ
Clock 6: ICM 7223 IPL Intersil Referring to FIGS. 4(a), 4(b) and 4(c), these figures collectively show a flow chart illustrating the operation of the apparatus for a "meal" program. As illustrated, the portion of the flow chart shown in FIG. 4(a) illustrates a "starting up" routine, followed by a "present credit display" showing the credits in each category and a "food code introduction" step. The portion of the flow chart shown in FIG. 4(b) concerns entering, displaying and checking the foof input data as well as displaying culmulative data, and, similarly to FIGS. 4(a) and 4(c), is self-explanatory. The portion of the flow chart shown in FIG. 4(c) provides for additional operations wherein a "forgotten" food can be added and recording of a "meal" is controlled, and including final storing steps and associated displays.

We claim:

1. A portable apparatus for acquiring and processing information relative to the diet of a person undergoing medical treatment, said apparatus comprising a portable unit comprising in combination:

(a) first inputting means for inputting
diet instructions, including a daily reference amount of proteids, lipids, glucids, alcohol and calories allowed to be ingested by the user, and treatment instructions in connection with a medical treatment;

(b) second inputting means, including a plurality of alphanumeric keys, for inputting dietetic information including the amount of each type of food intended or actually ingested by the user, information in connection with the health of a person using the apparatus, and information relative to any medical treatment actually performed;

(c) means for effectively inputting and refusing inputting the said dietetic information;

(d) at least one random access memory for storing the information inputted through the said first and second inputting means;

(e) clock means connected to said second inputting means for providing a date for each input to the said random access memory of information from said second inputting means and including dietetic information relative to the food actually ingested, the amount of glucose as measured and the treatment actually performed;

(f) at least one read only memory for storing data relative to a predetermined number of foods and including the average proteid, glucid, lipid, alcohol content of the food;

(g) a display means for displaying said information stored in the said random access memory and said data stored in said read only memory;

(h) computer means for receiving the inputted information stored is said random access memory and the data stored in said read only memory and for, responsive thereto, determining for each type of food as a function of the quantity of food inputted at one time through the said inputting means the amount of proteids, lipids, glucids, alcohol and calories, causing these amounts to be displayed on said displaying means and providing thereafter for storage of these amounts with an appropriate date in said random access memory, upon actuation of the said means for effectively inputting of information from said second inputting means, providing from time to time to a person using the apparatus appropriate information relative to the diet instructions and to the treatment instructions such as are initially inputted in the random access memory from said first inputting means, causing said daily reference amount of proteids, lipids, glucids, alcohol and calories to be displayed on the said displaying means and modifying the said reference amount as a function of the type and quantity of foods actually ingested and inputted through the second inputting means, and resetting the said amount of the maximum value of the said daily reference amount at a given time based upon the time information received from the clock means, for the next day;

(i) electric power supply means for powering the apparatus; and (j) connector means, adapted to connect said first inputting means and said random access memory to an external unit including a computer under doctor's control, for enabling initially inputting from the external unit the said diet instructions including the daily reference amount of proteids, lipids, glucids, alcohol and calories allowed to the user, for enabling initially inputting from the external unit the said treatment instructions and for enabling transferring to said external unit the said information inputted through the said second inputting means and stored in the said random access memory.

2. The apparatus of claim 1 further comprising means for connecting the said portable unit to an apparatus for automatically determining the amount of glucose in the blood and to input said value to the random access memory to be stored in the said random access memory with the date of said measurement as provided by the clock.

3. The apparatus as claimed in claim 1 wherein one of said keys comprises a meal key actuation of which controls processing of the inputted dietetic information in accordance with a dietetic program stored in said read only memory.

4. The apparatus as claimed in claim 1 wherein one of said keys comprises a glycemia key actuation of which provides processing of the inputted dietetic information in accordance with a program which relates to the glucose content of the blood and which is stored in the read only memory.

5. The apparatus as claimed in claim 1 wherein one of said keys comprises a medical treatment key actuation of which provides processing of the inputted dietetic information in accordance with a program stored in said read only memory relating to a particular medical treatment.

* * * * *